United States Patent [19]
Nelson et al.

[11] Patent Number: 5,919,213
[45] Date of Patent: Jul. 6, 1999

[54] DEFIBRILLATION TEST SYSTEM USING ACTUAL ICD HOUSING ELECTRODE

[76] Inventors: Randall S. Nelson, 7419 Pinehurst Ct., Pine Springs, Minn. 55115; Malcolm Drysdale, 8 Mount Way, Princess Risborough Buckinghamshire HP279BQ, United Kingdom

[21] Appl. No.: 08/716,686

[22] Filed: Sep. 16, 1996

[51] Int. Cl.$^6$ ...................................................... A61N 1/39
[52] U.S. Cl. .................................................................. 607/8
[58] Field of Search .................................... 607/1, 2, 4, 5, 607/8, 10, 33, 36, 37, 7, 27, 28

[56] References Cited

U.S. PATENT DOCUMENTS

| | | | |
|---|---|---|---|
| 5,095,903 | 3/1992 | DeBellis | 607/33 |
| 5,376,103 | 12/1994 | Anderson et al. . | |
| 5,385,574 | 1/1995 | Hauser et al. . | |
| 5,405,363 | 4/1995 | Kroll et al. . | |
| 5,411,539 | 5/1995 | Neisz . | |
| 5,454,837 | 10/1995 | Lindergren et al. | 607/4 |
| 5,679,022 | 10/1997 | Cappa et al. . | |

OTHER PUBLICATIONS

U.S. application No. 08/535,666, Kroll et al., filed Sep. 27, 1991.
U.S. application No. 08/475,861, Kroll et al., filed Jun. 6, 1991.

*Primary Examiner*—William E. Kamm
*Assistant Examiner*—George R. Evanisko
*Attorney, Agent, or Firm*—Brad Pedersen

[57] ABSTRACT

An intraoperative defibrillation test system for establishing defibrillation thresholds for an implantable cardioverter defibrillator (ICD) uses the actual ICD housing electrode, rather than a test housing electrode, as part of the test system. The intraoperative defibrillation test system includes the ICD, an external test station, and a test cable interconnecting the ICD with the test station. In one embodiment, the test cable is only connected to the ICD housing electrode and other test cables are used to connect to other implanted electrodes. In another embodiment, the test cable includes multiple conductors for connecting to all of the electrodes associated with the ICD, including the ICD housing electrode. In a further embodiment, the test cable includes a distal connector block that serves as a three-way T-between at least one port in a header of the ICD and an electrode lead.

10 Claims, 6 Drawing Sheets

Fig. 14

DEFIBRILLATION TEST SYSTEM USING ACTUAL ICD HOUSING ELECTRODE

FIELD OF THE INVENTION

The present invention relates to a defibrillation test system for an implantable cardioverter defibrillator (ICD). More particularly, the present invention relates to an intraoperative test system for establishing defibrillation thresholds for an ICD which uses the actual ICD housing electrode rather than a test housing electrode.

BACKGROUND OF THE INVENTION

Under existing medical practice, each time an implantable cardioverter defibrillator (ICD) is implanted in a human patient, an intraoperative testing procedure is attempted in order to determine a minimum defibrillation threshold (DFT) in terms of the number of joules of electrical energy required to successfully defibrillate a patient for the particular electrode lead combination which has been implanted in that patient. The intraoperative testing procedure involves inducing ventricular fibrillation in the heart and then immediately delivering a defibrillation countershock through the implanted electrode leads of a specified initial threshold energy, for example, 20 joules for a monophasic countershock. If defibrillation is successful, a recovery period is provided for the patient and the procedure is sometimes repeated one or more times using successively lower threshold energies until the defibrillation countershock is not successful or the threshold energy is lower than about 10 joules. If defibrillation is not successful, subsequent countershocks of the ICD's maximum output are immediately delivered to resuscitate the patient. After a recovery period, the procedure is repeated using a higher initial threshold energy, for example, 25 joules. It is also possible that during the recovery period prior to attempting a higher initial threshold energy, the electrophysiologist may attempt to lower the DFT for that patient by moving or changing the configuration of the electrodes.

The intraoperative testing procedure is designed to accomplish a number of objectives, including patient screening and establishing a minimum DFT for that patient. Typically, if more than 30 to 35 Joules are required for successful defibrillation with a monophasic countershock the patient is not considered to be a good candidate for an ICD. Otherwise the lowest energy countershock that results in successful defibrillation is considered to be the DFT for that patient. The use of the lowest energy possible for a defibrillation countershock is premised on the accepted guideline that a countershock which can defibrillate at a lower energy decreases the likelihood of damage to the cardiac tissue as well as provide the longest possible life for the device which has a finite amount of stored electrical energy with which to operate.

Traditionally, the intraoperative testing procedure has been accomplished by using an external test system which is connected to the implanted electrodes for delivering the test countershocks and also for delivering rescue countershocks in the event that a test countershock is unsuccessful. Once an appropriate DFT has been established for a given configuration of electrodes, the external test system is disconnected from the implanted electrodes and the actual ICD is connected to the implanted electrodes and then implanted in the patient.

Recent efforts to improve the efficiency of ICDs have led manufacturers to produce ICDs which are small enough to be implanted in the pectoral region, thereby enabling the housing of the ICD to form a subcutaneous electrode. Examples of ICDs in which the housing of the ICD serves as an optional addition electrode are described in U.S. Pat. Nos. 5,411,539 and 5,385,574. An example of a pectorally implanted ICD in which the housing is utilized as an electrode is described in U.S. Pat. No. 5,403,363. When the housing of the ICD is used as one of the electrodes, it is necessary to test that electrode as part of the intraoperative testing procedure.

Presently, all ICDs which have a housing electrode utilize some type of housing electrode emulator to perform the intraoperative testing procedure. One example of such a housing electrode emulator is disclosed in U.S. Pat. No. 5,411,539 which provides a largely reusable housing electrode emulator for screening patients for suitability for permanent implantation of such an ICD. The system disclosed in this patent has a reusable, sterilizable conductive can conforming to the dimensions of the ICD to be implanted. The reusable emulator has an electrical and mechanical attachment mechanism to connect to a standard lead and to the external test system. Once DFT testing is completed, the lead is disposed and the reusable emulator is removed and resterilized. Another example of a housing electrode emulator is disclosed in pending patent application Ser. No. 08/535,666, which describes a one piece, disposable pulse generator emulator for emulating a housing electrode of a pectorally implantable ICD. The emulator is connected by a permanently affixed lead an external test system to screen a patient for candidacy for an ICD. The one piece, disposable emulator has a housing that has substantially the same conductive geometry as does the desired ICD.

One alternative to the use of a housing electrode emulator would be to implant the ICD and utilize the ICD itself to deliver the test defibrillation countershocks for the intraoperative procedure. There are two disadvantages with this alternative. First, the use of the ICD to deliver the test defibrillation countershocks will necessarily reduce the overall energy stored in the ICD. This reduces the life of the device and decreases the total number of defibrillation countershocks which the device can deliver. Second, the delivery of any rescue shocks during the intraoperative procedure obviously cannot be accomplished using the ICD and must be initiated using an external defibrillator system. The use of an external defibrillator system is less desirable because of the larger amounts of energy required and the increased risk of tissue damage to the heart, as well as the possibility of damage to the ICD as result of delivery of a rescue shock from an external defibrillator system.

While the use of housing emulator electrodes for performing intraoperative testing prior to implantation of an ICD having a housing electrode are acceptable, the use of such housing emulator electrodes necessitates extra steps in the implantation procedure and increases the costs of the implantation procedure. Accordingly, it would be advantageous to provide an intraoperative test system for a pectorally implantable ICD which did not require the use of housing electrode emulator.

SUMMARY OF THE INVENTION

The present invention is an intraoperative defibrillation test system for establishing defibrillation thresholds for an implantable cardioverter defibrillator (ICD) which uses the actual ICD housing electrode, rather than a test housing electrode, as part of the test system. The intraoperative defibrillation test system includes the ICD, an external test station and a test cable interconnecting the ICD with the test station. In one embodiment, the test cable is only connected to the ICD housing electrode and other test cables are used to connect to other implanted electrodes. In another embodiment, the test cable includes multiple conductors for connecting to all of the electrodes associated with the ICD, including the ICD housing electrode. In a further embodiment, the test cable includes a distal connector block that serves as a three-way connection between at least one port in a header of the ICD and an electrode lead.

By utilizing the actual ICD housing electrode, rather than an emulation housing electrode, the present invention eliminates the steps associated with implantation and removal of the emulation housing electrode during the intraoperative test procedure. Additionally, by utilizing the actual ICD housing electrode, the present invention increases the confidence level of the defibrillation threshold (DFT) which is established by the intraoperative procedure. Finally, by utilizing an external test station to deliver the test defibrillation countershocks, rather than utilizing the ICD itself, the present invention does not degrade the overall energy storage capacity of the ICD.

DETAILED DESCRIPTION OF THE PREFERRED EMBODIMENT

Figure 1:
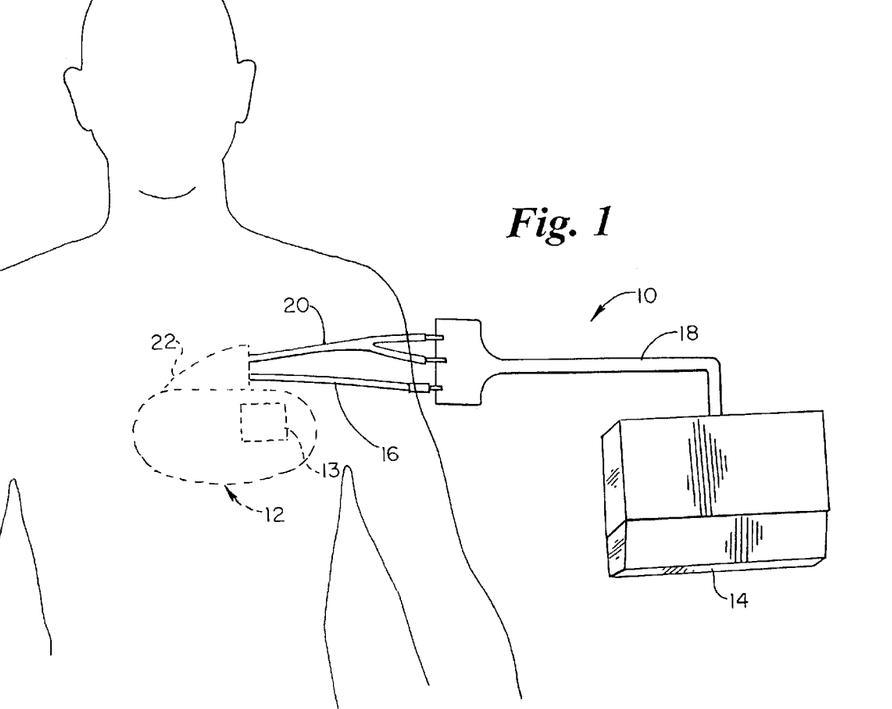
FIG. 1 is a pictoral view illustrating a preferred embodiment of an intraoperative defibrillation test system of the present invention.

Referring now to FIG. 1, a preferred embodiment of the present invention will now be described. An intraoperative defibrillation test system 10 in accordance with the present invention includes an implantable cardioverter defibrillator (ICD) 12, an external test station 14 and a test cable 16. In the embodiment shown in FIG. 1, test station 14 includes a patient cable 18 into which both test cable 16 and at least one electrode lead 20 which is connected to an implantable electrode (not shown) that can either be a transvenous electrode, an epicardial electrode or a subcutaneous electrode. The ICD 12 is a pectorally implantable ICD as known in the art with the modification as taught by the present invention. One example of a pectorally implantable ICD is the Sentinel™ ICD Model 2000 available from the assignee of the present invention and which is described, for example, in U.S. Pat. No. 5,405,363, although the present invention is equally applicable to any implantable ICD where the housing of the ICD is used as one of the defibrillation electrodes. External test station 14 is a defibrillation test system designed for the particular ICD, such as The SentinelTm Defibrillation Test System (DTS) Model 7001 available from the assignee of the present invention. The patient cable 18 is a cable capable of conducting sensing and defibrillation countershock signals between the test station 14 and the electrode leads 20, such as the Model 5006 Patient Cable available from the assignee of the present invention.

Preferably, test cable 16 is a single-use cable made of biocompatible material for short term implants (less than 1 hour) which is capable of delivering a minimum of 20 high energy defibrillation countershock of at least 750 volts and 50 joules. Test cable 16 must be compatible with appropriate sterilization standards. Preferably, test cable 16 is pre-packaged with ICD 12 in a durable sterile and shelf box packaging. Test cable 16 is used during an implantation procedure in order to establish defibrillation thresholds using the housing of the ICD 12 as one of the defibrillation electrodes. This allows for the advantageous use of ICD 12 as part of the testing procedure, rather than utilizing a separate test can electrode as is currently the accepted procedure.

Procedurally, a proximal end of test cable 16 is inserted into a port on the distal end of patient cable 18, and a distal end of test cable 16 is inserted into a CAN port or a separate test port of a header 22 of ICD 12. If required, separate port plugs (not shown) can be inserted into any unused ports of header 22 to seal the ports from fluid contamination. ICD 12 is then inserted into a pocket in the pectoral region of the patient created to receive the ICD 12. The remaining electrode leads 20 are inserted into the appropriate ports on the distal end of patient cable 18 and threshold testing is begun. Once testing is completed, the ICD 12 is removed from the pectoral pocket and the test cable 16 is removed, as well as any seal plugs when necessary. Electrode leads 20 are then inserted into the appropriate ports of header 22 of ICD 12, and then the ICD 12 is reinserted in the pectoral pocket of the patient.

Figure 2:
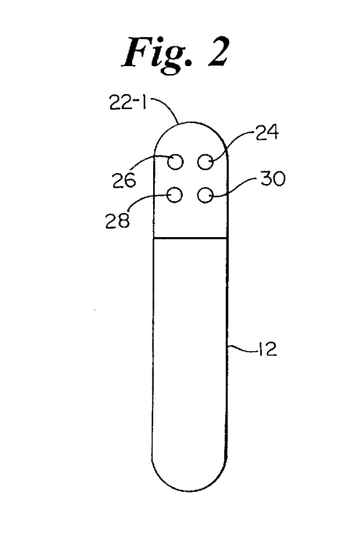
FIG. 2 is an end view of a first embodiment of a header of the ICD in accordance with the present invention.

FIG. 2 shows a header 22-1 of an ICD adapted for use with a first embodiment of test cable 16. Header 22-1 includes a CAN defibrillation port 24, two lead defibrillation ports 26, 28 and a pace/sense port 30. In this embodiment, the distal end of test cable 16 is inserted into the CAN defibrillation port 24. The advantage of this embodiment is that no changes are required to the standard header 22 of ICD 12 in order to accommodate the present invention.

Figure 3:
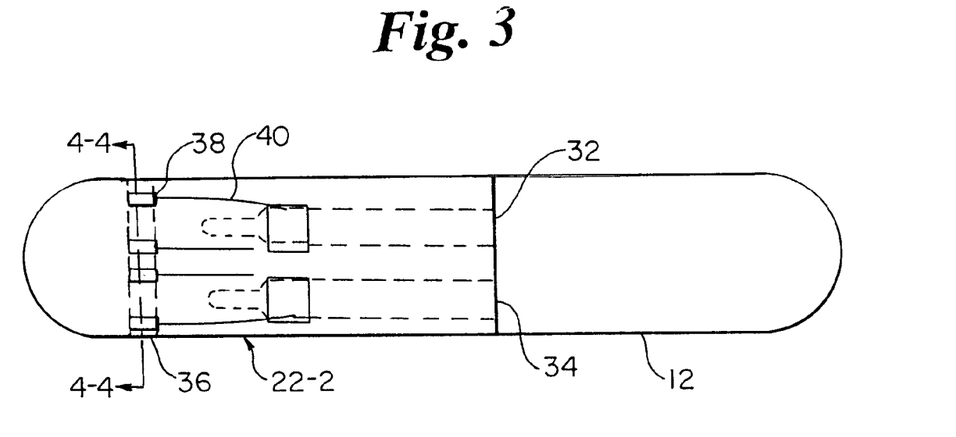
FIG. 3 is a top plan view of a second embodiment of a header of the ICD in accordance with the present invention utilizing a multiple contact.
Figure 4:
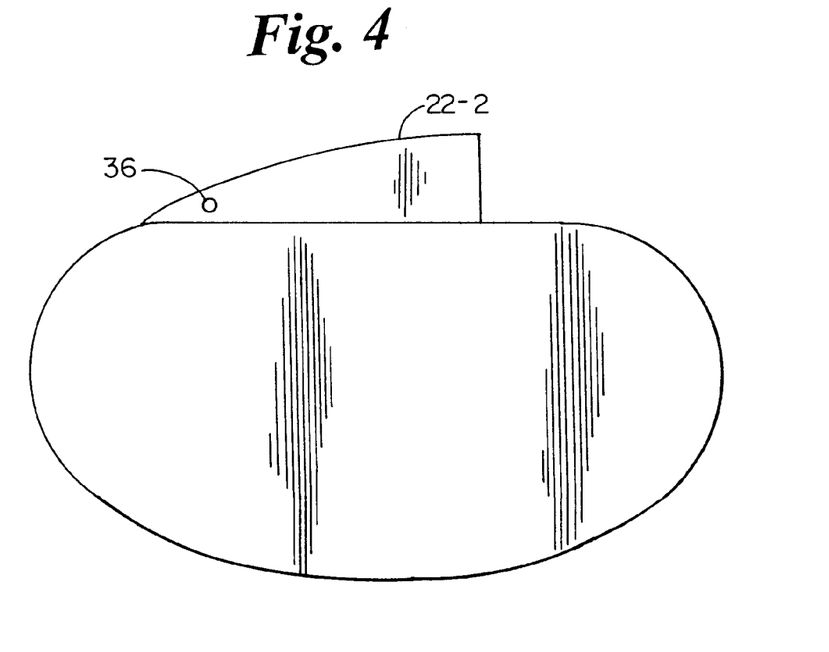
FIG. 4 is a side view of the second embodiment shown in FIG. 3.

FIGS. 3 and 4 show a header 22-2 of an ICD 12 adapted for use with a second embodiment of test cable 16. In this embodiment, header 22-2 includes at least two lead ports 32, 34 and a separate multi-contact testing port 36 having a plurality of internal test contact points 38. Preferably, testing port 36 is located in header 22-2 in a transverse orientation with respect to the longitudinal orientation of lead ports 32, 34, with electrical connections 40 internal to header 22-2 connecting selected test contact points 38 to given ports 32, 34. Other test contact points 38 may be connected to internal circuitry 13 within ICD 12 via feedthroughs between header 22-2 and ICD 12, or may be directly connected to the housing of ICD 12.

Figure 5:
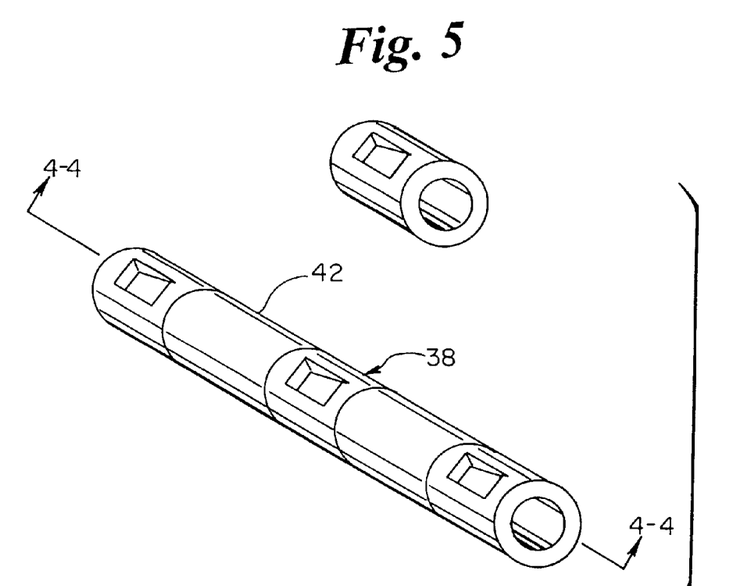
FIG. 5 is a detail perspective view of the multiple contact CAN test port shown in FIGS. 3 and 4.

FIG. 5 shows a preferred embodiment of the construction of a multi-contact testing port 36. In this embodiment, testing port 36 is constructed as a series of alternating insulator tubes 42 and contact point tubes 38 that are aligned coaxially. Preferably, contact point tubes 38 have an indentation or other structure which enhances a frictional fit of a corresponding protruding contact on the distal end of test cable 16 (not shown). Alternatively, a spring protusion or the like could be provided in port 36 to enhance the mechanical and electrical mating of multi-contact testing port 36.

Figures 6, 7:
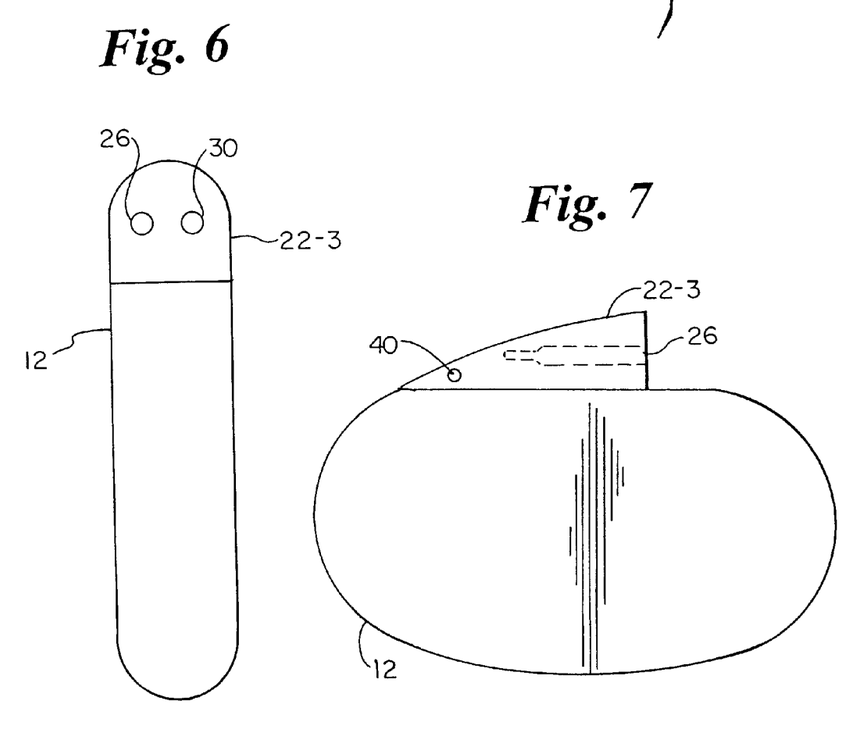
FIG. 6 is an end view of a third embodiment of the present invention utilizing a single contact CAN test port.
FIG. 7 is a side view of the third embodiment as shown in FIG. 6.

FIGS. 6 and 7 show another embodiment of a header 22-3 of an ICD 12 adapted for use with a third embodiment of test cable 16. Header 22-3 is much like header 22-2 except that contact testing port 40 is only electrically connected to the CAN housing electrode and is not connected to any other electrode leads 20 within header 22-3. This embodiment is particularly useful for a low profile ICD 12 in which there is only one defibrillation port 26 and one pace/sensing port 30 in the header 22-3.

Figure 8:
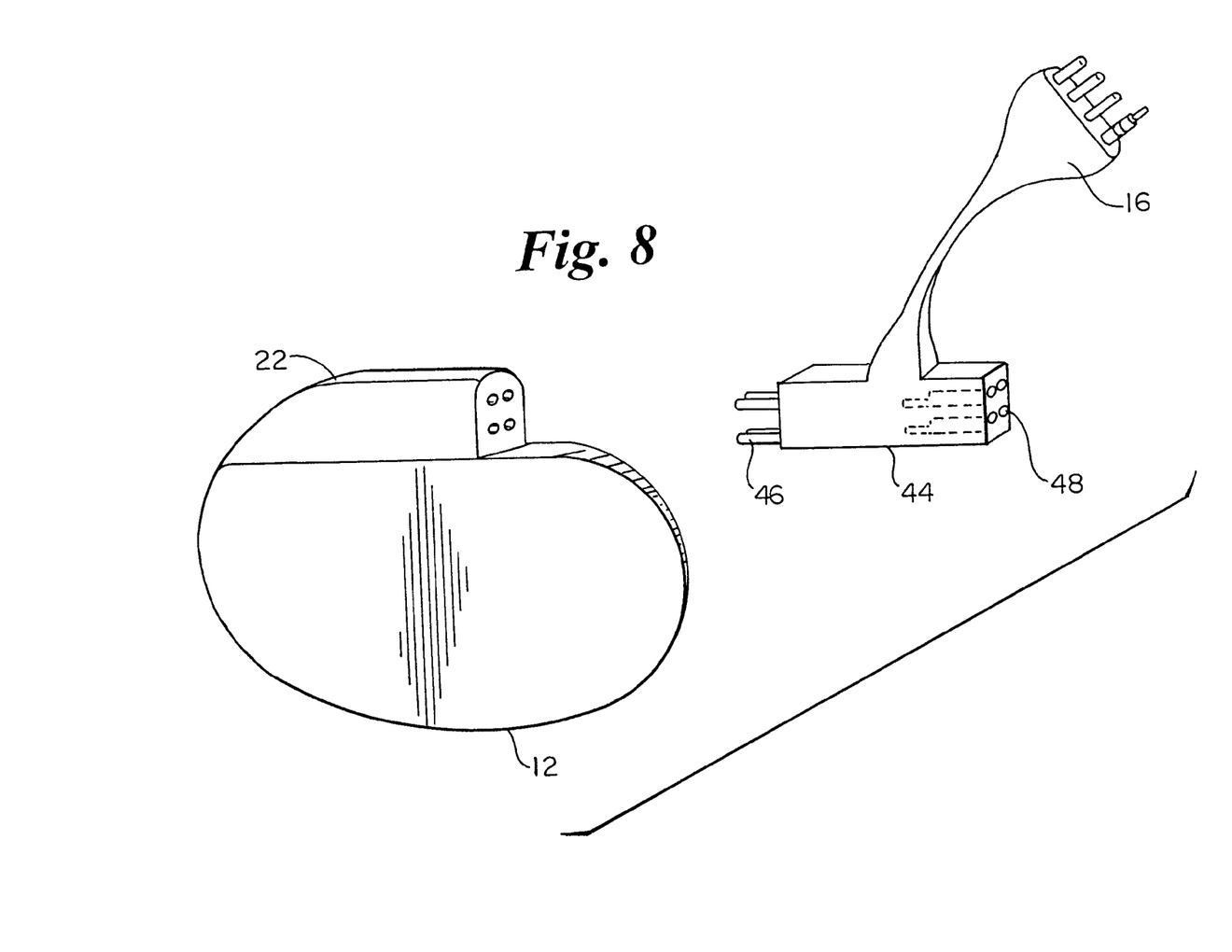
FIG. 8 is a perspective view of a fourth embodiment of the present invention including a three-way connector block.

FIG. 8 shows still another embodiment of the present invention wherein a T-connector 44 is used to accommodate both the standard connection to header 22 on one end and connection to electrode leads 22 on the other end, with the T-end connected to and/or integrated with the distal end of test cable 16. The advantage of this embodiment is that it is not necessary to extend electrode leads 20 out of the patient in order to connect those leads to the patient cable 18. T-connector 44 includes insertion pins 46 and insertion cavities 48, both of which are configured to match the ports of the particular header 22 of ICD 12.

Figure 9:
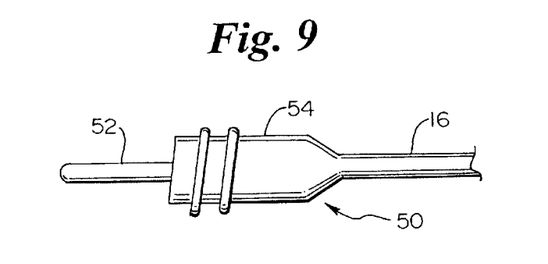
FIG. 9 is a side view of a test cable connector according to the first embodiment of the present invention shown in FIG. 2.

FIG. 9 shows a preferred embodiment of a connector 50 for the proximal end of test cable 16. Preferably, the connector 50 includes a stainless steel pin 52 extending beyond the cable 16 from a silicon boot or enlarged fitting 54 at the proximal end of test cable 16. It will be recognized that any number of electrical connectors could be utilized to accomplish connection of test cable 16 to either patient cable 18 or directly to DTS 14.

Figure 10:
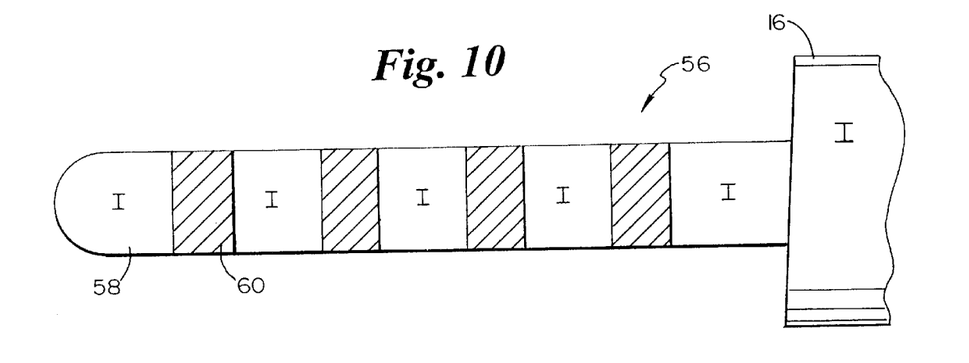
FIG. 10 is a side view of a test cable connector according to the second embodiment of the present invention shown in FIG. 3.

FIG. 10 shows a preferred embodiment of a multi-contact connector 56 for the distal end of test cable 16 specifically for use with the second embodiment of the present invention as shown in FIGS. 3, 4 and 5. In this embodiment, connector 56 consists of alternating bands of insulation material 58 and conductive material 60, with each of the conductive bands 60 being electrically connected to a corresponding conductor internal to test cable 16.

Figures 11, 12, 13:
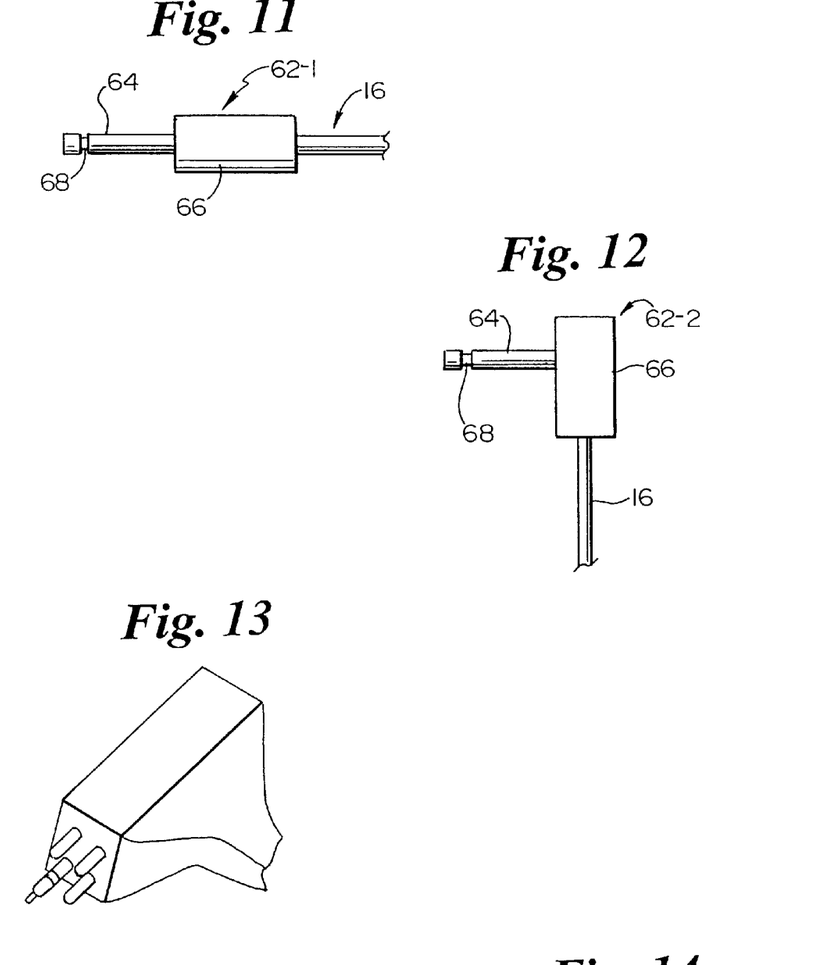
FIGS. 11 and 12 are side views of two alternate embodiments of a test cable connector for the third embodiment shown in FIG. 6.
FIG. 13 and 14 are individual views of pins and cavities shown in FIG. 8.
Figure 14:
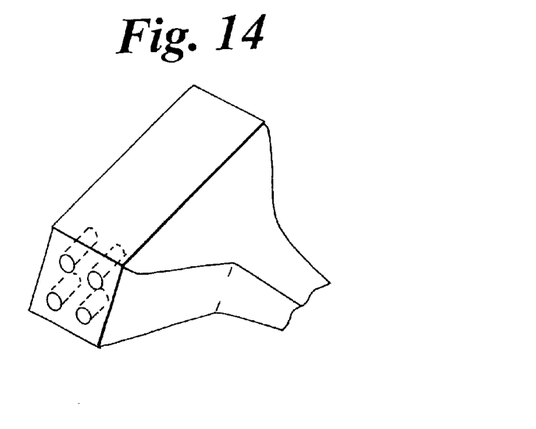

FIGS. 11 and 12 show a preferred embodiment of a single-contact connector 62 for the distal end of test cable 16 specifically for use with the third embodiment of the present invention as shown in FIGS. 6 and 7. As shown in FIG. 11, a stainless steel pin 64 extends either longitudinally, or as shown in FIG. 12, transversely, from the orientation of a silicon boot 66. Preferably, stainless steel pin 64 can include a physical indentation 68, or other physical feature, to aid in alignment and mechanical and electrical connection.

Preferably, the total length of test cable 16 is between 17 and 23 inches in length. Test cable 16 is preferably jacketed with silicone tubing which is bonded to the distal and terminal connectors to provide appropriate strain relief. Preferably, test cable 16 has a DC resistance of less than 1 ohm.

It will be apparent to those skilled in the art that numerous modifications and alternative embodiments of connector arrangements and choice of materials can be made without departing from the scope and spirit of the present invention.

What is claimed is:

1. An intraoperative defibrillation test system for establishing defibrillation thresholds for a patient for a given configuration of implantable electrodes within the patient, the test system comprising:

an implantable cardioverter defibrillator (ICD) for selectively delivering electrical defibrillation countershocks of between 0.5 and 35 joules through a plurality of implantable electrodes, at least one of the implantable electrodes being a housing electrode comprising at least a portion of a housing of the ICD;

an external test station for selectively delivering test electrical defibrillation countershocks of between 0.5 and 35 joules through the plurality of implantable electrodes, including the housing electrode and for selectively delivering rescue electrical defibrillation countershocks having a maximum energy of greater than 35 joules through the plurality of implantable electrodes; and a test cable interconnecting the test station with the plurality of implantable electrodes during an intraoperative test procedure in which the ICD is implanted in the patient and defibrillation threshold is established for the patient by delivering a test defibrillation countershock through the plurality of implantable electrodes, including the housing electrode.

2. The defibrillation test system of claim 1 wherein the test cable comprises a first test cable that is electrically connected from the test station only to the housing electrode of the ICD and a second test cable that is electrically connected from the test station to the other of the plurality of implantable electrodes.

3. The defibrillation test system of claim 1 wherein the test cable includes a plurality of electrical conductors within one cable, at least one conductor for each of the plurality of implantable electrodes, and wherein the test cable further includes a plurality of connectors which correspond to each of the conductors that are located on both ends of the one cable and by which each of the plurality of implantable electrodes are individually electrically connected to the test system.

4. The defibrillation test system of claim 1 wherein the ICD includes a header having at least one port adapted to receive a connector of an electrode lead, and wherein the test cable includes a connector on a distal end of the test cable that is adapted to mechanically and electrically interface with the at least one port.

5. The defibrillation test system of claim 1 wherein the ICD includes a header having at least one port adapted to receive a connector of an electrode lead, and wherein the test cable includes a three-way connector on a distal end of the test cable that is adapted to mechanically and electrically interface with the at least one port and with the connector of the electrode lead.

6. The defibrillation test system of claim 5 wherein the test cable includes a plurality of electrical conductors and a distal connector block which includes a plurality of the three-way connectors, each three-wave connector for interfacing with each port of the header.

7. The defibrillation test system of claim 1 wherein one of the plurality of implantable electrodes includes an electrode lead having a conductor on an end thereof, wherein the test cable includes a connector on a distal end thereof, and wherein the ICD includes a header having at least one first port adapted to receive the connector of the electrode lead and having a second port adapted to receive the connector on the distal end of the test cable.

8. The defibrillation test system of claim 7 wherein the second port on the header and the connector on the test cable each have multiple terminal connections.

9. The defibrillation test system of claim 8 wherein the multiple terminal connections of the second port are electrically connected to the housing electrode of the ICD and to the at least one first port on the header of the ICD such that all of the implantable electrodes are electrically connected through the ICD to the test station.

10. The defibrillation test system of claim 8 wherein the ICD includes therein control circuitry and at least one of the multiple terminal connections is electrically connected to the control circuitry within the ICD for communicating control signals between the control circuitry and the test station.

* * * * *